(12) United States Patent
Zeng et al.

(10) Patent No.: US 8,709,381 B2
(45) Date of Patent: Apr. 29, 2014

(54) COMPOUND CONTAINING A CARBON OR AN OXYGEN ISOTOPE, PREPARATION AND USE THEREOF, AND COMPOSITION COMPRISING THEREOF

(75) Inventors: Jun Zeng, Beijing (CN); Qiyin Sun, Beijing (CN)

(73) Assignee: Beijing Top Grade Medical Equipment Co., Ltd, Beijing (CN)

( * ) Notice: Subject to any disclaimer, the term of this patent is extended or adjusted under 35 U.S.C. 154(b) by 109 days.

(21) Appl. No.: 13/244,511

(22) Filed: Sep. 25, 2011

(65) Prior Publication Data

US 2012/0107238 A1    May 3, 2012

(30) Foreign Application Priority Data

Oct. 27, 2010   (CN) .......................... 2010 1 0527457

(51) Int. Cl.
*A61K 51/00*  (2006.01)
*C07H 15/24*  (2006.01)

(52) U.S. Cl.
USPC ........................................ 424/1.81; 536/18.1

(58) Field of Classification Search
None
See application file for complete search history.

(56) References Cited

U.S. PATENT DOCUMENTS

2008/0240330 A1 * 10/2008 Holden .......................... 376/190
2010/0312118 A1 * 12/2010 Horzewski .................... 600/458

OTHER PUBLICATIONS

Blokland et al, Positron emission tomography: a technical introduction for clinicians, European Journal of Radiology, 2002, vol. 44, pp. 70-75.*

* cited by examiner

*Primary Examiner* — Michael G Hartley
*Assistant Examiner* — Sun Y Kim
(74) *Attorney, Agent, or Firm* — Cooper Legal Group, LLC

(57) ABSTRACT

The present disclosure relates to a compound comprising at least one of a carbon or an oxygen isotope and a process for preparing the compound. The process comprises irradiating a compound comprising at least one of a carbon or an oxygen atom using photons or particles having an energy in the range of 20 MeV-430 MeV. The carbon and/or the oxygen atom is then allowed to be converted into a carbon and/or an oxygen positron nuclide through a photonuclear reaction. Provided that the molecular structure of the compound is not disrupted, the compound comprising the carbon and/or the oxygen isotope is prepared. The compound may be used in positron and/or other nuclide imaging to obtain a distribution and/or metabolic image of the compound in a human and/or animal body.

6 Claims, No Drawings

COMPOUND CONTAINING A CARBON OR AN OXYGEN ISOTOPE, PREPARATION AND USE THEREOF, AND COMPOSITION COMPRISING THEREOF

RELATED APPLICATION

This application claims priority to Chinese Application No.: 201010527457.X, filed on Oct. 27, 2010, entitled "A COMPOUND CONTAINING A CARBON OR AN OXYGEN ISOTOPE, PREPARATION AND USE THEREOF, AND COMPOSITION COMPRISING THEREOF," at least some of which may be incorporated herein.

FIELD

The present disclosure relates to a compound comprising at least one of a carbon or an oxygen isotope and preparation thereof. It also relates to use of is the compound in positron or other nuclide imaging and/or use of the compound in obtaining a distribution or metabolic image in an organism. It also relates to a composition comprising the compound.

BACKGROUND

Nuclear medicine imaging techniques, which are represented by positron emission tomography (hereinafter "PET"), digital scintillator detector (hereinafter "DS") and single photon emission computed tomography (hereinafter-"SPECT"), for example, are effective in the diagnosis of diseases, including heart disease and cancer. These techniques involve administration of labeled tracers with a specific radioisotope (hereinafter "radiopharmaceutical"), followed by detecting γ-rays emitted from the tracers. Nuclear medicine imaging techniques have been widely used in medicine because of their high specificity and sensitivity to diseases. Such techniques also generally provide a high degree of information about diseases, compared to other diagnostic techniques.

In recent years, a series of radioactive halogen-labeled compounds, including [$^{18}$F]1-amino-3-fluorocyclobutanecarboxylic acid (hereinafter "[$^{18}$F]FACBC"), have been discovered and developed as radiopharmaceuticals, and their clinical application is under investigation (e.g., Japanese Patent Laid-open No. 2000-500442; Jonathan McConathy et al., "Improved synthesis of anti-[$^{18}$F]FACBC: improved preparation of labeling precursor and automated radiosynthesis", Applied Radiation and Isotopes, (Netherlands). 2003, 58, p. 657-666; and Timothy M. Shoup et al., "Synthesis and Evaluation of [$^{18}$F]1-Amino-3-fluorocyclobutane-1-carboxylic Acid to Image Brain Tumors.", The Journal of Nuclear Medicine, 1999, 40, p. 331-338). [$^{18}$F]FACBC is considered to be effective as a diagnostic tracer for highly proliferative tumors because it has a property of being taken up specifically by an amino acid transporter.

The process for preparing [$^{18}$F]FACBC comprises: providing 1-(N-(t-butoxy-carbonyl)amino)-3-[((trifluoromethyl)-sulfonyl)oxy]-cyclobutane-1-carboxylic acid methyl ester as a labeling precursor; substituting the triflate group at position 3 of the precursor with a radioactive fluorine; and carrying out deprotection by subjecting the resulting compound to an acidic condition (e.g., Japanese Patent Laid-open No. 2000-500442; Jonathan McConathy et al., "Improved synthesis of anti-[$^{18}$F]FACBC: improved preparation of labeling precursor and automated radiosynthesis", Applied Radiation and Isotopes, (Netherlands). 2003, 58, p. 657-666; and Timothy M. Shoup et al., "Synthesis and Evaluation of [$^{18}$F]1-Amino-3-fluorocyclobutane-1-carboxylic Acid to Image Brain Tumors.", The Journal of Nuclear Medicine, 1999, 40, p. 331-338).

However, the cost of preparing a compound labeled with [$^{18}$F] is high, and the compound labeled with [$^{18}$F] is limited to specific compounds (e.g., the compound cannot be labeled until some groups in the compound are substituted by a fluorine or a carbon).

DESCRIPTION

The systems and/or techniques described herein provide for, among other things, a compound comprising at least one of a carbon or an oxygen isotope (e.g., also referred to as a labeled compound comprising at least one of a carbon or an oxygen atom, or referred to as a compound labeled with at least one of a carbon or an oxygen isotope) and a process for preparation thereof. The systems and/or techniques described herein also provide for the use of the compound in positron imaging and/or the use of the compound in obtaining a distribution or metabolic image in an animal and/or a human body. The systems and/or techniques described herein further provide for a composition comprising the compound.

In one embodiment, a process for preparing a compound comprising at least one of a carbon or an oxygen isotope is provided. The process is characterized by utilizing photons or particles having an energy in the range of 20 MeV to 430 MeV (e.g., generated by a high energy electron accelerator and/or or a proton, a heavy ion, and/or a neutron treatment device) to irradiate a compound comprising at least one of a carbon or an oxygen atom. The process also comprises allowing the carbon and/or the oxygen atom in the compound to be converted into a carbon and/or an oxygen positron nuclide, respectively, through is a photonuclear reaction(s). In this way, provided that the molecular structure of the compound is not disrupted, the compound comprising at least one of the carbon or the oxygen isotope may be prepared.

Compounds comprising at least one of a carbon or an oxygen atom can be treated according to the process described above to generate positron nuclides such as $^{11}$C or $^{15}$O, for example, and a compound comprising an isotope such as a carbon, oxygen and/or other isotope can be prepared. When the compound comprising the isotope is injected into a body, a distribution and/or metabolic image of the compound in the body can be acquired (e.g., using PET and/or other nuclear medicine imaging techniques), and distribution and/or metabolic information about the compound can be utilized for clinical diagnostic purposes and/or for biomedical research, for example.

In other words, the process of the present disclosure is not merely applicable to compounds containing $^{18}$F but also to other compounds comprising an element such as carbon or oxygen, and detection of the compound can be done conveniently and quickly.

According to another embodiment, the at least one carbon or oxygen positron nuclide is $^{11}$C or $^{15}$O, respectively, which is generated by irradiating the compound comprising at least one of the carbon or the oxygen atom. That is, a $^{12}$C of a compound comprising a carbon element can be converted to $^{11}$C and a $^{16}$O of a compound comprising an oxygen element can be converted to $^{15}$O until the energy of a ray reaches a predetermined level. There are a variety of carbon and oxygen isotopes, and it is preferred in one embodiment that the carbon or oxygen isotope is one with a similar number of neutrons as that of $^{12}$C or $^{16}$O.

In addition, it has been found that the conversion from $^{12}$C to $^{11}$C and/or $^{16}$O to $^{15}$O can be achieved if the energy of a high-energy ray is between 20 MeV and 430 MeV (e.g., million electron volts). Such a conversion technique can be applied to prepare $^{11}$C and/or $^{15}$O-labeled tracers for nuclear medicine.

According to yet another embodiment, the compound comprising at least one of the carbon or the oxygen isotope is a drug or other chemical used in humans and/or animals.

It will be appreciated that commonly used drugs (e.g., comprising a compound comprising an element such as carbon and/or oxygen) that are administered to humans and/or animals such as adriamycin, cefoperazone sodium, glucose, porphyrin and pamidronate disodium can be used in the preparing process disclosed herein. For example, adriamycin, cefoperazone sodium, glucose, porphyrin and/or pamidronate disodium can be intravenously injected in humans and/or animals.

The labeled compound comprising the isotope, such as a carbon or an oxygen isotope, for example, and a process for preparing the labeled compound may have the following beneficial effects:

1. Using a photonuclear reaction mode which is different from the present isotope-preparing process to generate the positron nuclides such as $^{11}$C or $^{15}$O;

2. Different from the present labeling technology, no complicated labeling technology is required;

3. Suitable for the labeling of compounds comprising an element such as carbon or oxygen, no limitation to the structure of such compound;

4. Not changing the chemical structure of a compound when being labeled;

5. Carrying out positron imaging quickly after the irradiation, operating easily and simply;

6. Labeling the combinatorial library of compounds with different structures, and high throughput screening in-vivo at the same time;

7. Short half life of nuclides of $^{11}$C or $^{15}$O positron, low radioactive pollution after imaging, being friendly to the environment;

8. Can be used to provide a drug for positron imaging of PET and/or DS;

9. Can be used in clinical studies and preclinical research or development of medicine, which can shorten the cycle of examination and development, and thus save on costs associated therewith.

According to another embodiment, a labeled compound comprising an isotope such as a carbon or an oxygen isotope can be prepared using the processes described above.

When the compound comprising the isotope (e.g., prepared according to the aforementioned techniques) is injected into a human and/or an animal body, a distribution or metabolic image of the compound in the body can be obtained by methods such as PET, for example. Generally, distribution and/or metabolic information related to the compound will be presented clearly on the distribution and/or metabolic image.

According to another embodiment, a composition comprising a labeled compound comprising the isotope (e.g., such as carbon or oxygen isotope) can be created.

In one embodiment, the composition further comprises a pharmaceutically acceptable carrier or excipient. For example, the composition may comprise a pharmaceutically acceptable carrier or excipient to satisfy requirements of pharmaceuticals and/or examinations.

In yet another embodiment, the compound comprising the isotope (e.g., such as a carbon or an oxygen isotope) may be used in positron or other nuclide imaging.

During the process of imaging, the composition can comprise a pharmaceutically acceptable carrier or excipient.

Further, in still another embodiment, the compound comprising the isotope (e.g., such as a carbon or an oxygen isotope) can be used in obtaining a distribution and/or metabolic image in humans and/or animals.

It will be appreciated that compounds comprising an element such as carbon or oxygen can be irradiated by X-rays, proton rays, neutron rays and/or heavy ions rays with an energy of 20-430 MeV to generate positron nuclides, such as $^{11}$C or $^{15}$O, for example, and a compound comprising an isotope such as a carbon or an oxygen isotope can be prepared. If the compound comprising the isotope is injected into a human and/or an animal body, a distribution or a metabolic image of the compound comprising the isotope in the body can be obtained by imaging methods (e.g., PET). Moreover, in such an image, distribution and metabolic information of the compound may be presented clearly.

By way of example, organic compounds and bio-molecules comprise elements such as a carbon atom(s) ($^{12}$C atom). When the energy of X rays, proton particles, neutron particles and/or heavy ion particles reach a predetermined level (usually 20 MeV or more), a neutron in the atomic nucleus of $^{12}$C, $^{16}$O, and/or other atoms with a large photon capture cross-section will be knocked out by a photon, and therefore generate positron nuclides, such as $^{11}$C or $^{15}$O, for example. Such a procedure may be referred to as a photonuclear reaction (e.g., $^{12}$C(gamma,n)$^{11}$C). After the photonuclear reaction, the compound is spontaneously labeled by the positron nuclides, such as $^{11}$C or $^{15}$O, and a labeled compound with little to no difference in structure is prepared. The positron nuclides, such as $^{11}$C or $^{15}$O, may release a gamma photon(s) (γ photon) with an energy of 511 KeV, for example, in opposite directions through capturing the surrounding electrons and a pair of gamma photons can be imaged on a positron imaging device.

The general process of labeling the compound comprising an element, such as carbon includes: placing a compound comprising an element such as carbon or a composition thereof to be labeled into a qualified package. It is noted during this phase that the sample must contain little to no water. The sample is placed into a vessel such as a lead jar, and subsequently placed onto the exit of the rays. Before the sample is irradiated, the cap of the lead jar is open or the sample is placed into a specific device. Then the sample is irradiated using rays with an energy of 20 MeV or more, preferably 30 MeV or more (e.g., where the dosage of the irradiation depends upon the desired/required amount of energy).

Herein are provided several examples to further clarify one or more of the techniques and/or systems described herein.

Example 1

Example 1 relates to an experiment utilizing adriamycin of an anti-tumor drug on a myocardial injury.

The details of the procedure of the present example are as follow: 3 mg of adriamycin is irradiated by 50 MV of photons with a dosage of 30 Gy (gray). After irradiation, it is shown by the fluorescence analysis that there is no change in the structure of adriamycin after the irradiation. A $^{12}$C atom of the adriamycin molecule is converted into a $^{11}$C positron nuclide and an $^{16}$O atom therein is converted into a $^{15}$O positron nuclide. It was found that the adriamycin accumulates at the heart after a tail vein injection of adriamycin comprising the $^{11}$C positron nuclide and the $^{15}$O positron nuclide into SD rats (outbreeding rat).

Example 2

Example 2 relates to a study on distribution of an anti-inflammatory drug in vivo.

Cefoperazone sodium is a pro-inflammatory focus antibiotic. After it is irradiated by photons of 50 MV with a dosage of 30 Gy (gray), a $^{12}C$ atom of the cefoperazone sodium molecule is converted into a $^{11}C$ positron nuclide and an $^{16}O$ atom therein is converted into an $^{15}O$ positron nuclide. When injecting the cefoperazone labeled with $^{11}C$ and $^{15}O$ into the body, it has been shown from PET/CT (e.g., CT being short for computer tomography) imaging that the cefoperazone accumulates in the right leg of the SD rats suffering with inflammatory, and almost no cefoperazone accumulates in the control left leg.

Example 3

Example 3 relates to an in vivo metabolism study of glucose in the rat.

Glucose is one of the main compounds providing energy for cells. After it is irradiated by photons of 50 MV with a dosage of 30 Gy (gray), a $^{12}C$ atom of the glucose molecule is converted into an $^{11}C$ positron nuclide and a $^{16}O$ atom therein is converted into an $^{15}O$ positron nuclide. When injecting the glucose labeled with $^{11}C$ and $^{15}O$ into the body, it has been shown from PET/CT imaging that the glucose is metabolized in cardiac muscle, skeletal muscle and liver. The metabolite is excreted from the kidney to the urinary bladder.

Example 4

Example 4 relates to a study of imaging of porphyrin synthesis in-vivo.

Porphyrin plays an important role in an organism. It is important for the study of physiological conditions, biochemical condition, and diseases to know the porphyrin synthesis in vivo. 5-ALA is a precursor of the porphyrin synthesis. After it is irradiated by photons of 50 MV with a dosage of 30 Gy (gray), a $^{12}C$ atom of the 5-ALA molecule is converted into an $^{11}C$ positron nuclide and a $^{16}O$ atom therein is converted into an $^{15}O$ positron nuclide. When injecting the 5-ALA labeled with $^{11}C$ and $^{15}O$ into the body, it has been shown from the PET/CT imaging that the liver is the main organ of porphyrin synthesis.

The structure of 5-ALA is as follow:

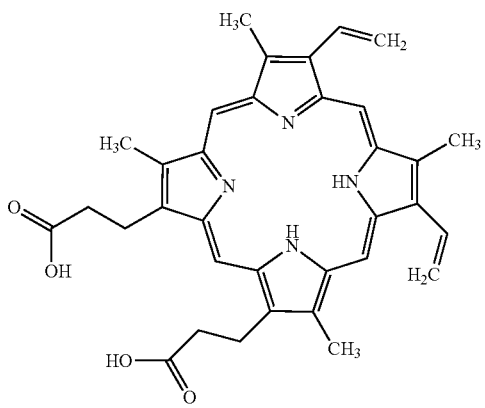 [SMILES: C=CC1=C(C)c2cc3nc(cc4[nH]c(cc5[nH]c(cc1n2)c(C)c5C=C)c(C)c4CCC(=O)O)C(CCC(=O)O)=C3C]

Example 5

Example 5 relates to a study on skeletal metabolism.

Phosphonic acids can participate in skeletal metabolism, recovery of skeletal injury, inflammation remission, and play a role in analgesic effect. Bonin is a common clinical drug for pain relief of skeletal injury. After it is irradiated by photons of 50 MV with a dosage of 30 Gy, a $^{12}C$ atom of the Bonin molecule is converted into a $^{11}C$ positron nuclide and an $^{16}O$ atom therein is converted into a $^{15}O$ positron nuclide. When injecting the Bonin labeled with $^{11}C$ and $^{15}O$ into the body, it has been shown from PET/CT imaging that the Bonin is mainly distributed in the skeletal.

According to the above examples, it can be seen that the imaging of a distribution of a variety of drugs in animal bodies can be made by the labeled compound comprising carbon, which is convenient for the drug development and clinical diagnosis.

It will be appreciated that the conversion can be adjusted properly, so that a $^{12}C$ atom of the compound can be converted to a $^{11}C$ positron nuclide and/or a $^{16}O$ atom therein can be converted to a $^{15}O$ positron nuclide more efficiently. There is no special requirement as long as the effects of labeling are similar to those described herein.

What is claimed is:

1. A process, comprising:
utilizing at least one of high energy photons or high energy particles having an energy in the range of 20 MeV-430 MeV generated by at least one of a high energy electron accelerator, proton treatment device, heavy ion treatment device, or neutron treatment device to irradiate a compound comprising at least one of a carbon atom or an oxygen atom, wherein the compound comprising at least one of a carbon atom or an oxygen atom is at least one of adriamycin, cefoperazone sodium, glucose, porphyrin, or pamidronate disodium; and at least one of:
allowing the carbon atom to convert into a carbon positron nuclide through a photonuclear reaction, a molecular structure of the compound comprising at least one of a carbon atom or an oxygen atom not disrupted, thereby preparing a compound comprising a carbon isotope, or allowing the oxygen atom to convert into an oxygen positron nuclide through the photonuclear reaction, the molecular structure of the compound comprising at least one of a carbon atom or an oxygen atom not disrupted, thereby preparing a compound comprising an oxygen isotope.

2. The process of claim 1, the carbon positron nuclide being $^{11}C$ and the oxygen positron nuclide being $^{15}O$.

3. The process of claim 1, at least one of:
the compound comprising a carbon isotope being a drug used in at least one of humans or animals, or
the compound comprising an oxygen isotope being a drug used in at least one of humans or animals.

4. The process of claim 3, the compound comprising a carbon isotope prepared as a $^{11}C$-tracer and the compound comprising an oxygen isotope prepared as a $^{15}O$-tracer.

5. The process of claim 1, comprising at least one of:
using the compound comprising a carbon isotope in nuclide imaging, or
using the compound comprising an oxygen isotope in nuclide imaging.

6. The process of claim 1, comprising at least one of:
using the compound comprising a carbon isotope in obtaining at least one of a distribution image or a metabolic image of the compound comprising a carbon isotope in at least one of a human body or an animal body, or
using the compound comprising an oxygen isotope in obtaining at least one of a distribution image or a metabolic image of the compound comprising an oxygen isotope in at least one of a human body or an animal body.

* * * * *